US010232047B2

(12) United States Patent
Prasad et al.

(10) Patent No.: US 10,232,047 B2
(45) Date of Patent: Mar. 19, 2019

(54) TOPICAL OIL COMPOSITION FOR THE TREATMENT OF FUNGAL INFECTIONS

(71) Applicant: VYOME BIOSCIENCES PVT LTD., Delhi (IN)

(72) Inventors: Sudhanand Prasad, Delhi (IN); Nilu Jain, Delhi (IN); Sumana Ghosh, Delhi (IN); Suresh Chawrai, Delhi (IN)

(73) Assignee: VYOME BIOSCIENCES PRIVATE LIMITED, New Delhi (IN)

( * ) Notice: Subject to any disclaimer, the term of this patent is extended or adjusted under 35 U.S.C. 154(b) by 0 days.

(21) Appl. No.: 14/366,755

(22) PCT Filed: Dec. 20, 2012

(86) PCT No.: PCT/IB2012/057512
§ 371 (c)(1),
(2) Date: Jun. 19, 2014

(87) PCT Pub. No.: WO2013/093823
PCT Pub. Date: Jun. 27, 2013

(65) Prior Publication Data
US 2014/0364440 A1  Dec. 11, 2014

(30) Foreign Application Priority Data
Dec. 20, 2011 (IN) .......................... 3746/DEL/2011

(51) Int. Cl.
*A61K 8/36* (2006.01)
*A61K 8/37* (2006.01)
*A61K 8/41* (2006.01)
*A61K 8/49* (2006.01)
*A61Q 5/00* (2006.01)
*A61Q 17/00* (2006.01)
*A61K 47/44* (2017.01)
*A61K 9/00* (2006.01)
*A61K 47/06* (2006.01)
*A61K 47/10* (2017.01)
*A61K 47/14* (2017.01)
*A61K 47/24* (2006.01)
*A61K 8/31* (2006.01)
*A61Q 3/02* (2006.01)
*A61K 8/34* (2006.01)
*A61K 8/58* (2006.01)
*A61K 8/67* (2006.01)
*A61K 8/92* (2006.01)
*A61K 47/12* (2006.01)
*A61K 47/22* (2006.01)

(52) U.S. Cl.
CPC .............. *A61K 47/44* (2013.01); *A61K 8/31* (2013.01); *A61K 8/342* (2013.01); *A61K 8/347* (2013.01); *A61K 8/361* (2013.01); *A61K 8/37* (2013.01); *A61K 8/4926* (2013.01); *A61K 8/4973* (2013.01); *A61K 8/585* (2013.01); *A61K 8/678* (2013.01); *A61K 8/92* (2013.01); *A61K 9/0014* (2013.01); *A61K 47/06* (2013.01); *A61K 47/10* (2013.01); *A61K 47/12* (2013.01); *A61K 47/14* (2013.01); *A61K 47/22* (2013.01); *A61K 47/24* (2013.01); *A61Q 3/02* (2013.01); *A61Q 5/006* (2013.01); *A61Q 17/005* (2013.01)

(58) Field of Classification Search
CPC ...... A61K 8/361; A61K 8/4926; A61K 47/12; A61K 47/22; A61K 9/0014; A61K 8/37; A61K 8/375; A61K 8/41; A61K 8/411; A61K 8/496; A61K 8/4973; A61K 8/4986; A61K 8/49; A61Q 5/006; A61Q 17/005
See application file for complete search history.

(56) References Cited

U.S. PATENT DOCUMENTS

| | | | |
|---|---|---|---|
| 4,406,884 A | 9/1983 | Fawzi et al. | |
| 4,711,902 A | 12/1987 | Serno | |
| 5,198,209 A | 3/1993 | Zhou et al. | |
| 5,447,729 A | 9/1995 | Belenduik et al. | |
| 5,461,068 A * | 10/1995 | Thaler .................. | A61K 9/0014 514/399 |
| 5,569,461 A | 10/1996 | Andrews | |
| 5,624,666 A | 4/1997 | Coffindaffer et al. | |
| 5,681,802 A * | 10/1997 | Fujiwara ................ | A61K 8/466 510/130 |
| 5,698,219 A | 12/1997 | Valdivia et al. | |
| 5,739,152 A | 4/1998 | Andersson et al. | |
| 5,980,947 A | 11/1999 | Yamakawa et al. | |
| 6,011,067 A | 1/2000 | Hersh | |
| 6,110,908 A * | 8/2000 | Guthery ................. | A01N 31/02 514/188 |

(Continued)

FOREIGN PATENT DOCUMENTS

EP          64830   * 11/1982  ........... A61K 31/415
EP     0116439 A2    8/1984
(Continued)

OTHER PUBLICATIONS

Liu et al. Mycopathologia 2008, 166, 93-102.*
(Continued)

*Primary Examiner* — Irina Neagu
(74) *Attorney, Agent, or Firm* — David S. Resnick; Nixon Peabody LLP

(57) ABSTRACT

The present invention is directed to anti-fungal compositions comprising an anti-fungal agent, an oil and excipients or additives. The compositions of the present invention are devoid of C-11 or greater fatty acids/esters.

20 Claims, 3 Drawing Sheets

(56) References Cited

U.S. PATENT DOCUMENTS

| | | | |
|---|---|---|---|
| 6,410,593 | B1 | 6/2002 | De Mesanstourne et al. |
| 6,485,743 | B1 | 11/2002 | Jung et al. |
| 6,638,621 | B2 | 10/2003 | Anderson |
| 6,939,829 | B1 | 9/2005 | Watson et al. |
| 7,198,794 | B1 | 4/2007 | Riley |
| 7,547,752 | B2 | 6/2009 | Bailey et al. |
| 9,138,429 | B2 | 9/2015 | Wise et al. |
| 2002/0106461 | A1 | 8/2002 | Talton |
| 2002/0176894 | A1 | 11/2002 | Lee et al. |
| 2003/0068389 | A1 | 4/2003 | Hiramoto et al. |
| 2004/0202636 | A1 | 10/2004 | Kaczvinsky et al. |
| 2004/0248901 | A1* | 12/2004 | Lee ............... A61K 9/1075 514/254.07 |
| 2004/0266852 | A1 | 12/2004 | Coleman |
| 2005/0118276 | A1 | 6/2005 | Lei et al. |
| 2006/0210622 | A1 | 9/2006 | Pace et al. |
| 2008/0193508 | A1* | 8/2008 | Cohen ............... A61K 8/36 424/447 |
| 2008/0311201 | A1 | 12/2008 | Der-Yang et al. |
| 2009/0123507 | A1 | 5/2009 | Ohrlein et al. |
| 2009/0253645 | A1 | 10/2009 | Ponikau |
| 2009/0281197 | A1* | 11/2009 | Kinsinger ............ A61K 8/347 514/729 |
| 2010/0016271 | A1 | 1/2010 | Chang et al. |
| 2011/0195944 | A1 | 8/2011 | Mura et al. |
| 2012/0027875 | A1 | 2/2012 | Melman |
| 2012/0087959 | A1 | 4/2012 | Khopade et al. |
| 2012/0171272 | A1 | 7/2012 | Premachandran et al. |
| 2012/0309843 | A1* | 12/2012 | Buyuktimkin ....... A61K 9/0017 514/655 |
| 2013/0011452 | A1 | 1/2013 | Loupenok |
| 2013/0059929 | A1 | 3/2013 | Koehler et al. |
| 2016/0058775 | A1* | 3/2016 | Prasad ............... A61K 8/342 424/401 |

FOREIGN PATENT DOCUMENTS

| | | |
|---|---|---|
| EP | 1060732 A2 | 12/2000 |
| EP | 1923043 A1 | 5/2008 |
| JP | 11-1433 A | 1/1999 |
| JP | 2000189129 A | 7/2000 |
| JP | 2002-275007 A | 9/2002 |
| JP | 2003-238310 A | 8/2003 |
| JP | 2005-206538 A | 8/2005 |
| JP | 2011032212 A | 2/2011 |
| WO | 96/15774 A1 | 5/1996 |
| WO | 0197799 A1 | 12/2001 |
| WO | 03/044145 A1 | 5/2003 |
| WO | 2005/007139 A2 | 1/2005 |
| WO | 2005/032489 A2 | 4/2005 |
| WO | 2005/123103 A1 | 12/2005 |
| WO | 2010/038066 A1 | 4/2010 |
| WO | 2010/083337 A2 | 7/2010 |
| WO | 2011/009083 A1 | 1/2011 |
| WO | 2011124241 A2 | 10/2011 |
| WO | 2012/017349 A2 | 2/2012 |
| WO | 2012/037424 A1 | 3/2012 |
| WO | 2013/108410 A1 | 7/2013 |

OTHER PUBLICATIONS

Futterer J. Soc. Cosmet. Chem. 1981, 32, 327-338.*
Chudasama et al. J. Adv. Pharm. Technol. Res. 2011, 2(1), 30-38.*
Bachhav et al. AAPS PharmSciTech 2009, 10 (2), 476-481.*
Skrypzak, W., et al., "Piroctone Olamine-Ein Vielseitiges Antischuppenmittel", SOFW-Journal Seifen, Oele, Fette, Wachse, Verlag Fur Chemische Industrie, Augsburg, DE, 117(15): 577-584 (1991).
International Search Report in International Application No. PCT/IB2012/057512 dated Jun. 20, 2013.
Bergsson et al., "In Vitro Killing of Candida albicans by Fatty Acids and Monoglycerides" Antimicrobial Agents and Chemotherapy 45(11):3209-3212 (2001).
Chadeganipour et al., "Antifungal activities of pelargonic and capric acid on microsporum gypseum" Mycoses 44:109-112 (2001).
Chua et al., "A modified mycological medium for isolation and culture of Malassezia furfur" Malaysian J. Pathol 27(2):99-105 (2005).
Kabara and Marshall, "Medium-Chain Fatty Acids and Esters" Antimicrobials in Food, 3rd Edition, CRC Press, Boca Raton, FL—pp. 327-360.
Faergemann et al., "In vitro Activity of R126638 and Ketoconazole Against *Malassezia* Species" ACTA Derm Venereol 86:312-315 (2006).
Wiegand et al., "Agar and broth dilution methods to determine the minimal inhibitory concentration (MIC) of antimicrobial substances" Nature Protocols 3(2):163-175 (2008).
Hsieh M.H., et al., Diagn. Microbiol. Infect. Dis. 16(4):343-349 (1993). "Synergy assessed by checkerboard. A critical analysis."
Meletiadis, J. et al., Antimicrobial Agents and Chemotherapy 54(2):602-609 (2010). doi: 10.1128/AAC.00999-09. Epub Dec. 7, 2009. "Defining Fractional Inhibitory Concentration Index Cutoffs for Additive Interactions Based on Self-Drug Additive Combinations, Monte Carlo Simulation Analysis, and In Vitro-In Vivo Correlation Data for Antifungal Drug Combinations against Aspergillus fumigatus.".
Zhang, H. et al., New J. Chem. 39:5776-5796 (2015). DOI: 10.1039/C4NJ01932F "Synthesis of novel sulfonamide azoles via C—N cleavage of sulfonamides by azole ring and relational antimicrobial study."
Chen et al., "The biology of Malassezia organisms and their ability to induce immune responses and skin disease", Veterinary Dermatology 16:4-26 (2005).
Deangelis et al., "Three Etiologic Facets of Dandruff and Seborrheic Dermatitis: Malassezia Fungi, Sebaceous Lipids, and Individual Sensititivity", Journal of Investigative Dermatology Symposium Proceedings 10(3):295-297 (2005).
Trueb R., "Shampoos: Ingredients, efficacy and adverse effects", JDDG: Journal der Deutschen Dermatologischen Gesellschaft 5(5):356-365 (2007).
Verma et al., "Particle size of liposomes influences dermal delivery of substances into skin", International Journal of Pharmaceutics 258:141-151 (2003).
Yao et al., "How Bacterial Pathogens Eat Host Lipids: Implications for the Development of Fatty Acid Synthesis Therapeutics", The Journal of Biological Chemistry 290(10):5940-5946 (2015).

* cited by examiner

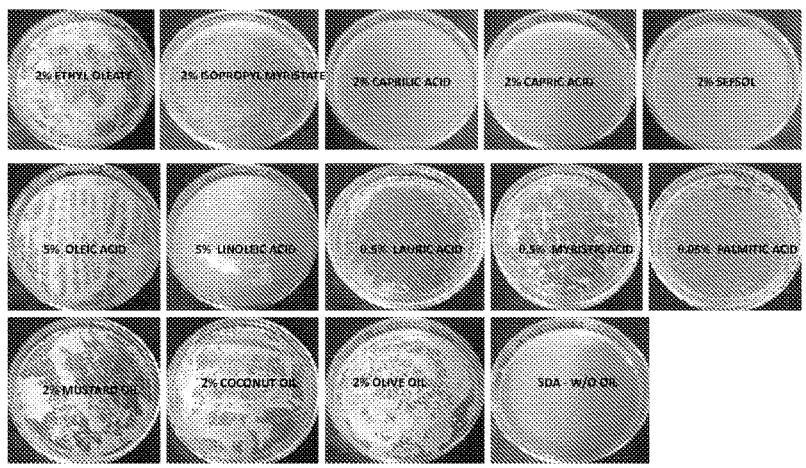
Fig. 1: Picture showing growth/no growth of M.furfur depending on the nutrients provided in culture media

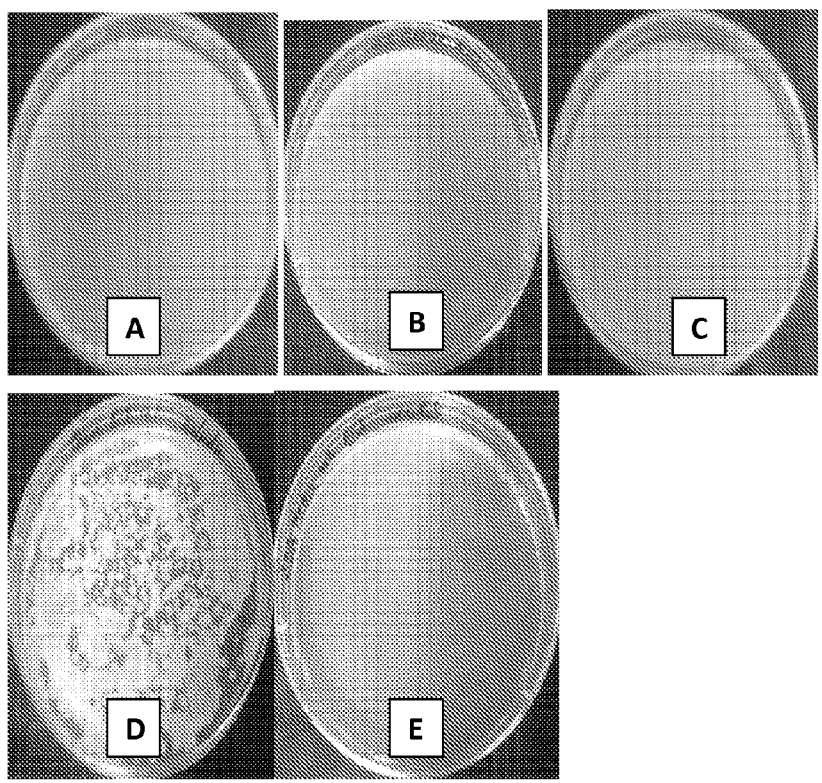
Fig. 2: Picture showing growth/no growth of M.furfur depending on the nutrients provided in culture media at concentration 2% (A) Caprylic acid (C-8) (B) Capric acid (C-10) (C) Sefsol 218 (mono caprylate of propylene glycol) (D) Olive oil and (E) without any oil suppliment

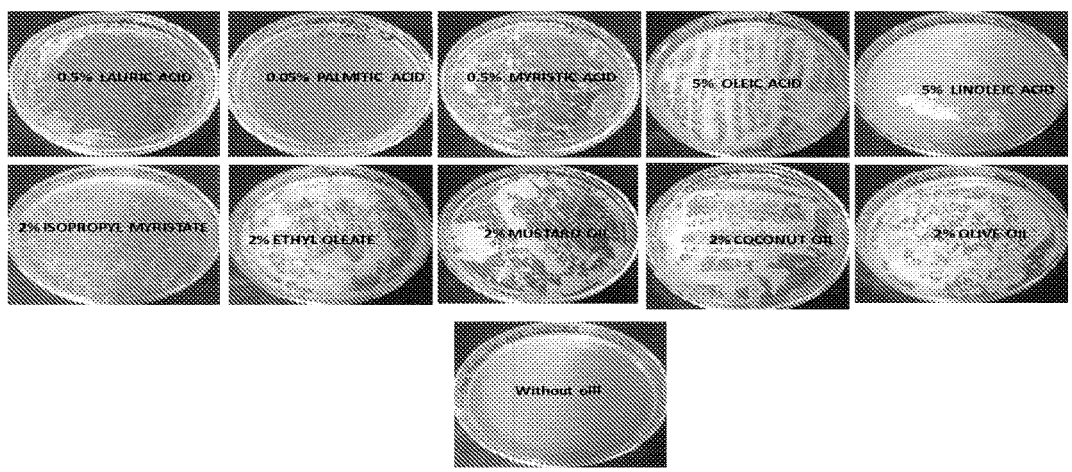
Fig.3: Picture showing growth of *M.furfur* depending on the nutrients provided in culture media

US 10,232,047 B2

TOPICAL OIL COMPOSITION FOR THE TREATMENT OF FUNGAL INFECTIONS

CROSS REFERENCE TO RELATED APPLICATIONS

This application is a 35 U.S.C. § 371 National Phase Entry Application of International Application No. PCT/IB2012/057512 filed Dec. 20, 2012, which designates the U.S., and which claims benefit under one or more of 35 U.S.C. § 119(a)-119(d) of Indian Patent Application No. 3746/DEL/2011, filed Dec. 20, 2011, the content of which is incorporated herein by reference in its entirety.

FIELD OF THE INVENTION

The present invention provides topical compositions comprising an antifungal agent, an oil and excipients or additives, for the treatment of fungal infections. The present invention further provides compositions devoid of more than C-10 fatty acids or their esters for the treatment of topical fungal infections. The present invention further provides antifungal compositions comprising an antifungal agent, a fatty acid or its ester with less than C11 chain length and excipients or additives.

BACKGROUND OF THE INVENTION

Fungal infections of the skin are also known as 'mycoses'. They are common and generally mild. In sick or otherwise immune-suppressed individuals, however, fungi can sometimes cause serious disease. Fungal infections in humans range from superficial, i.e., skin surface to deeply invasive type or disseminated infection.

In general, superficial fungal infections (also known as cutaneous mycosis) can affect the outer layers of skin, nails and hair. The main groups of fungi causing superficial fungal infections are dermatophytes (tinea), yeasts, e.g., candida, malassezia, piedra, etc. and moulds. These infections include dandruff/seborrheic dermatitis (D/SD), ringworm, onychomysis, intertrigo, and those in psoriasis amongst others.

Seborrheic dermatitis is a common, chronic, superficial skin disorder causing scaly, itchy, red skin on the scalp, eyebrows, nasolabial creases, lips, ears, sternal area, axillae, submammary folds, umbilicus, groins, and gluteul crease. The disease is characterized by many shapes, sizes, and surface textures and is often crust-like, yellowish, and accompanied by itching. Seborrheic dermatitis is one of the leading causes of stubborn dandruff and occurs in all age groups. This condition primarily affects the sebaceous cysts present in the skin.

Currently, fungi of the genus *Malassezia* are believed to be the most likely responsible agents for causing dandruff (Dawson T. L., *J. Investig. Dermatol. Symp. Proc.* (2007), 12:1519). Most cases of seborrhoeic dermatitis likely involve an inflammatory reaction to the proliferation of the yeast *Malassezia*. These fungi are highly dependent on external lipids for in vitro growth (Chen T. A. and Hill P. V., *Vet Dermatol*, (2005), 16:4). Further, the inability to synthesize fatty acids may be complimented by the presence of multiple secreted lipases to aid in utilizing host lipids. Consequently, these fungi metabolize triglycerides present in sebum through these lipases resulting in lipid by-products. Penetration of the top layer of the epidermis, the stratum corneum, by these lipid by-products results in an inflammatory response in susceptible persons, which disturbs homeostasis causing erratic cleavage of stratum corneum cells, further leading to dandruff and seborrheic dermatitis.

The most common treatment of fungal infections is the topical application of antifungal agents that reduce the level of *Malassezia* on the scalp. Maintaining the scalp clean is mandatory for sufferers of seborrheic dermatitis. Use of effective anti-dandruff shampoos is, therefore, a significant way of preventing this condition.

Typically, the antifungal agent is applied to the scalp as a component of a shampoo or other hair care composition. The disadvantage of such shampoo formulations is that during normal usage the formulation does not remain on the scalp for a period of time sufficient to allow the antifungal agent to achieve its maximal therapeutic effect (Ralph M. Trüeb, *JDDG*, (2007), 5:356). These are designed to be applied, for example, in the shower or bath, and shortly thereafter rinsed off with water. Typically, the application instructions for such shampoos suggest that the formulation be removed after 3-5 minutes.

One of the antifungal agents, ketoconazole is among the most potent and widely used in anti-dandruff shampoos. However, the exposure time of shampoo is less, due to which the efficacy is poor and relapse rates are higher.

In the past we found that, fatty acids and their derivatives (e.g. methylated and hydroxyl fatty acids) are known to possess antibacterial and antifungal activity as they target the cell membrane leading to increase in membrane fluidity (Douglas and Marshalland, "Antimicrobials in Food", $3^{rd}$ edition, CRC Press 2005 Pg. no. 327-360).

In context to another review, the pelargonic and capric acid on *Microsporum gypseum* were found to be effective when tested in-vitro cell culture (Chandeganipour and Haims, "Mycoses", 2001, Volume 44, Issue 3-4, pages 109-112). Similar reports were found with reference to *Candida albicans* when exposed to monoesters of glycerides of capric (C10 saturated medium chain fatty acid) (Bergsson et al., Antimicrobial agents and Chemotherapy, 2001, Vol 45 pg. no. 3209-3212).

U.S. Patent Application 2010/0016271 discloses hair conditioning compositions comprising cationic surfactant, triglyceride oil and an anti-dandruff agent. These compositions contain triglyceride oil, which are fatty acid esters of glycerol, and hence act as nutrients and aid in the growth of the fungus. These compositions contain fatty material up to 10% having carbon chains from 8 to 30 carbon atoms.

U.S. Pat. No. 5,624,666 describes shampoo compositions containing anionic surfactants, cationic polymers, and zinc pyridinethione as an anti-dandruff agent. It describes that conditioning agents such as silicone fluids can optionally be incorporated into the compositions therein. Head & Shoulders® Dandruff Shampoo Plus Conditioner is an example of a marketed product which provides both anti-dandruff and conditioning benefits upon application of the shampoo to hair. The exposure time of shampoos is less than required for effective antifungal activity, hence relapse rates are higher.

U.S. Pat. No. 7,547,752 refers to synergistic combination of an anti-dandruff agent with conjugated linoleic acid for prevention or treatment of dandruff and scalp itching.

European Patent No. 1923043A1 discloses cationic conditioning agents and an anti-dandruff agent with surfactants, silloxanes and natural and lipophillic oily components and their derivatives for the treatment or prevention of dandruff with conditioning.

European Patent No 0116439 discloses fatty acids like petroselinic and linoleic and saturated and unsaturated derivatives which alleviate dandruff and stimulate hair growth.

Commercially available formulations for the treatment of dandruff are leave-on hair formulations such as hair oils, styling gels, etc. These formulations also contain anti-dandruff or antifungal agents. Conventional leave-on formulations, especially oils or creams, contain fatty acid or their esters as an essential ingredient. These fatty acid and esters aid the growth of dandruff-causing fungus (*Malassezia furfur*) and work as nutrients.

Accordingly, there remains a need for an antifungal composition that provides improved cleansing and optimal anti-dandruff efficacy. The present invention addresses this need by providing topical compositions having antifungal agents and is devoid of fungus nutrients.

OBJECTIVE OF THE INVENTION

The primary objective of the invention is to provide antifungal compositions comprising an antifungal agent, an oil and excipients or additives, for the treatment of fungal infections Yet another objective of the invention is to provide antifungal compositions devoid of more than C-10 fatty acids or their esters for the treatment of topical fungal infections.

BRIEF DESCRIPTION OF THE DRAWINGS

FIG. 1 is a photograph showing the effect of nutrients provided in the culture media on the growth of *M. Furfur*

FIG. 2 is a photograph showing the effect of 2% caprylic acid (C8) (A), 2% Capric acid (C10), (B) and 2% monocaprylate of propylene glycol (C). Olive oil (D) and no oil supplement (E) were used as controls.

FIG. 3 is a photograph showing the growth of *M. furfur* depending on the nutrients provided in the culture media.

BRIEF DESCRIPTION OF THE TABLES

Table 1: Piroctone olamine—oil compositions
Table 2: Ketoconazole—oil compositions
Table 3: Results of MIC for oil compositions of piroctone olamine
Table 4: Results of MIC for oil compositions of ketoconazole
Table 5: Oil compositions containing piroctone olamine as antifungal agent
Table 6: MIC of oil compositions containing piroctone olamine against *M. furfur*
Table 7: MIC for oil compositions containing piroctone olamine against *M. obtuse*
Table 8: Oil compositions containing ketoconazole as antifungal agent
Table 9: Oil compositions containing piroctone olamine and ketoconazole in combination
Table 10: Oil compositions containing piroctone olamine as antifungal agent and Minoxidil
Table 11: Gel compositions containing antifungal agents devoid of C-11 or greater fatty acids/esters
Table 12: Zone of inhibition of gel compositions containing piroctone olamine against *M. furfur*
Table 13: Preparation of cream compositions containing antifungal agents Piroctone olamine or ketoconazole.

SUMMARY OF THE INVENTION

The present invention provides antifungal compositions that are devoid of C-11 or greater fatty acids and their esters as these fatty acids/esters serve as nutrients for the growth of the fungus. The present invention further provides topical antifungal oil compositions that eliminate existing dandruff on the scalp, or prevent or reduce relapse of dandruff formation. The present invention further provides antifungal compositions comprising an antifungal agent, a fatty acid or its ester with less than C-11 chain length, and excipients or additives.

DETAILED DESCRIPTION OF THE INVENTION

While the invention is susceptible to various modifications and alternative forms, specific aspect thereof has been shown by way of example and drawings and will be described in detail below. It should be understood, however that it is not intended to limit the invention to the particular forms disclosed, but on the contrary, the invention is to cover all modifications, equivalents, and alternative falling within the spirit and the scope of the invention as defined by the appended claims.

The Applicants would like to mention that the examples are mentioned to show only those specific details that are pertinent to understanding the aspects of the present invention so as not to obscure the disclosure with details that will be readily apparent to those of ordinary skill in the art having benefit of the description herein.

In the following detailed description of the aspects of the invention, reference is made to the accompanying drawings and graphs that form part hereof and in which are shown by way of illustration specific aspects in which the invention may be practiced. The aspects are described in sufficient details to enable those skilled in the art to practice the invention, and it is to be understood that other aspects may be utilized and that charges may be made without departing from the scope of the present invention. The following description is, therefore, not to be taken in a limiting sense, and the scope of the present invention is defined only by the appended claims.

Accordingly the present invention is directed to compositions for the treatment of fungal infections, comprising:
(A) at least one antifungal agent;
(B) at least one oil and;
(C) at least one excipient
where said composition being devoid of C-11 fatty acids and their esters.

Another aspect of the present invention is to provide an anti dandruff oil composition comprising:
(A) at least one antifungal agent;
(B) at least one C10 or lower fatty acid or its ester; and
(C) at least one excipient.

Yet another aspect of the present invention is to provide methods for the treatment of fungal infections comprising administering to a patient in need thereof an antifungal composition of the present invention.

Antifungal agent as used herein includes, but is not limited to piroctone olamine, ciclopirox olamine, ketoconazole, climbazole, miconazole nitrate, itraconazole, fluconazole, econazole, terconazole, saperconazole, amorolfine, oxiconazole, clotrimazole, luliconazole, terbinafine, butenafine, naftifine, selenium disulfide, salicylic acid, sulfur, tar preparations, capric acid and derivatives, caprylic acid and derivatives, zinc pyrithione, hinokitol, and chemical compounds from natural sources, such as extract of arnica, walnut shells, tea tree oil, rosemary oil, birch. Other antifungal agents known to the art-skilled may also be used in the compositions of the present invention.

In one embodiment, the antifungal agent used in the composition of the present invention is piroctone olamine. In another embodiment, the antifungal agent is ketoconazole. In yet another embodiment of the present invention, the composition comprises a combination of piroctone olamine and ketoconazole.

The amount of antifungal agent used in the compositions of the present invention is in the range of from about 0.01% to about 10% by weight of the total composition. In one embodiment, the antifungal agent is in the range of from about 0.01% to about 5% by weight of the total composition. In a further embodiment, the antifungal agent is in the range of about 0.01% to about 2% by weight of the total composition.

Oil as used herein includes, but is not limited to, paraffin oil, silicone oils, terpenes, fatty alcohols, dibutyl adipate, dioctyl adipate, fatty acids/esters (devoid of more than C10-) or a combination thereof.

As used herein, less than C11 fatty acid and/or its ester includes, but is not limited to propionic acid, butyric acid, pentanoic acid, hexanoic acid, heptanoic acid, caprylic acid, nonanoic acid, capric acid, Mono/di ester of these acids with propylene glycol, mono/di/tri esters of these acids with glycerol, and combinations thereof.

Essential oils as used herein include, but are not limited to, natural and synthetic oils such as eucalyptus oil, rosemary oil, pine needle oil, tea tree oil, sage oil, cinnamon oil, lemon oil, lime oil, orange oil, peppermint oil, spearmint oil, wintergreen oil, sweet birch oil, clove leaf oil, camphor oil, cardamon oil, cedar leaf oil, sweet birch oil and others known to the art-skilled.

The amount of oil used in the compositions of the present invention is in the range of about 0.5% to about 99% by weight of the total composition, more preferably 50% to 99% when formulated as oil, 5% to 50% when formulated as cream/ointment or 0.5% to 20% when formulated as gel/serum/spray.

As used herein, excipient includes, but is not limited to, solvents, surfactants and additives used in pharmaceutical and cosmetic formulations. The amount of excipients used in the compositions of the present invention is in the range of about 0.5% to about 99% by weight of the total composition.

Solvents as used herein include, but are not limited to, C-1 to C-6 lower aliphatic alcohols, such as, for example, ethanol, isopropyl alcohol, butanol and the like, lower alkyl acetate, ethers, carboxylic acid and derivatives containing carbon chain length less than C11 (caprylic acid, capric acid and the like) or mixture/s thereof, fatty alcohols such as undecanol, oleyl alcohol, lauryl alcohol or combinations thereof.

Additives as used herein include, but are not limited to, thickeners, antioxidants, perfumes/fragrances, essential oils, pH adjusters, herbal extracts, preserving agents, hair conditioning substances, hair care adjuncts, skin care adjuncts, emollient, dyestuffs, moisturizers, vitamins, sphingoceryls, sunscreens, surfactants, oil-soluble polymers which are compatible with the base oil and/or skin care agents including skin-nutrient agents, anti-wrinkle agents, light and dust protectors.

For example, compositions of the present invention may contain additives such as thickeners (for example, bentonite, cellulose and the like), antioxidants (for example, butylated hydroxytoluene (BHT), butylated hydroxyanisole (BHA), tert-butylhydroquinone (TBHQ), ferulic acid, Vitamin A, Vitamin E (Tocopherol)), preservatives (for example, methyl p-hydroxybenzoate or propyl p-hydroxybenzoate, sorbic acid and the like), hair care ingredients (for example, fatty alcohols, peptides, proteins, vitamins and mixtures thereof), light protective agents or sunscreens (for example, p-methoxycinamic acid isoamyl ester and the like).

Surfactants as used herein include, but are not limited to, ceteareths, ceteth, isoceteths, laureths, oleths, steareths, lauramide DEA, linoleamide DEA and other surfactants which are suitable for topical application.

As used herein, pH adjusters include, but are not limited to, inorganic or organic acids (e.g., citric acid, lactic acid, succinic acid, acetic acid, fumaric acid, glycolic acid, benzoic acid), bases, salts and/or buffers thereof.

Herbal extracts as used herein include, but are not limited to, Amla fruit extract, Arnica Extract, Brahmi extract and others known to the art-skilled.

Hair care adjuncts as used herein include, but are not limited to, ingredients beneficial in the treatment of hair loss or the promotion of hair growth such as taurine, caffeine, minoxidil, azelaic acid, marine cartilage, hydrolysed keratin, biotin, niacin, panthenol, vitamin B6, zinc, copper, peptides, horsetail silica, beta sitosterols, pycnogenol, PABA, green tea extract, folic acid, iron, L-cysteine, magnesium, ginseng and others known to the art-skilled.

Skin care adjuncts as used herein include, but are not limited to, those that are beneficial for the treatment of various skin conditions (like dry skin, oily skin, fine lines, pigmentation, etc.) such as proteins, vitamins (e.g., A, B, C, D, E, and K), trace metals (e.g., zinc, calcium and selenium), moisturizers (e.g., emollients, humectants, film formers, occlusive agents, and agents that affect the natural moisturization mechanisms of the skin), LTV absorbers (physical and chemical absorbers such as paraminobenzoic acid (PABA), titanium dioxide, zinc oxide, etc.), anti-irritants (e.g., steroids and non-steroidal anti-inflammatories), botanical extracts (e.g., aloe vera, chamomile, cucumber extract, ginkgo biloba, ginseng, and rosemary), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, skin conditioning agents (e.g., aloe extracts, allantoin, bisabolol, ceramides, dimethicone, hyaluronic acid, and dipotassium glycyrrhizate) and other natural components (e.g., oatmeal) known to the art-skilled.

In yet another embodiment of the present invention, the topical anti-dandruff hair oil composition comprising:

(a) antifungal agent selected from the group consisting of piroctone olamine, ketoconazole, zinc pyrithione or combination thereof; wherein said antifungal agent is present in the range of 0.01% to about 10%, more preferably in the range of 0.01% to 5%, more preferably in the range of 0.01% to 2% by weight of the total composition.

(b) oil selected from the group consisting of paraffin oil, salicylic acid, capric acid and derivatives, caprylic acid and derivatives, fatty acid or esters having carbon chain length less then C-10 or a combination thereof wherein said oil is present in the range of 1% to 99%;

(c) solvent selected from the group of lower aliphatic alcohols, lower alkyl acetate, ethers, carboxylic acid or derivatives containing carbon chain length less than C11, fatty alcohols or a combination thereof; and (d) additive selected from the group of thickener, antioxidant, perfume/fragrance, essential oil, pH adjuster, herbal extract, preserving agent, hair conditioning substance, hair care adjunct, skin care adjunct, skin care agent, skin-nutrient agent, emollient, dyestuff, moisturizer, vitamin, sphingoceryl, sunscreen, surfactant, oil-soluble polymer, anti-wrinkle agent, light or dust protector or a combination thereof.

In yet another embodiment of the present invention provides methods for the treatment of fungal infections comprising administering to a patient in need thereof an antifungal composition of the present invention, said composition comprising at least one antifungal agent, at least one oil and at least one excipient, said composition being devoid of C11 or higher fatty acids and their esters. The term "treatment" covers any topical fungal treatment in a mammal, such as a human.

The topical compositions of the present invention are used in the treatment of diseases associated with *Malassezia* including, but not limited to, tinea pedis, tinea capitis, tinea cruris, tinea glabrosa, tinea corporis, onychomycosis, pityriasis capitis, pityriasis vesicolor, pityrosporum folliculitis, seborrheic dermatitis. Compositions of the present invention are also used in the treatment of diseases associated with other fungi like *Trychophyton rubrum* or *Trychophyton mentagrophytes* or *Microsporum* species, or *Epidermophyton* species, or *Candida albicans*, etc. and other nondermatophyte molds.

The compositions of the present invention are also of veterinary use in the topical treatment of dermatological fungal infections.

Compositions of the present invention provide better retention and penetration of antifungal agent onto the hair, skin, scalp and nails. Accordingly, the present invention provides compositions and methods of treating fungal infections of the skin, scalp, hair or nail. In one embodiment of the present invention, the antifungal composition is topical hair oil. In another embodiment, the antifungal composition of the present invention is anti-dandruff oil. In yet another embodiment, the composition of the present invention is a hair gel. In a further embodiment, the composition of the present invention is a nail varnish.

The compositions of the present invention can be in the form of oils, creams, lotions, serums, gels, ointments, foams, sprays or aerosols.

The following examples serve to further illustrate the present invention and are not to be construed to limit the scope of the present invention.

EXAMPLES

Example 1

Preparation of Various Oil Compositions Containing Piroctone Olamine

The compositions were prepared by dissolving the active agent in ethanol or isopropyl alcohol (IPA). The oleyl alcohol was then added and stirred until a homogenous solution was obtained. Other excipients or additives were added and stirred to get clear solution except liquid paraffin. Weight was finally made up with liquid paraffin and stirred until homogenous solution was obtained. Final formulations were clear transparent oil solutions. Table 1 describes anti-fungal clear oil compositions containing piroctone olamine as anti-fungal agent using various excipients or additives.
Result:
1. Compositions using liquid paraffin as base oil containing piroctone olamine, were clear oil solutions.
2. Addition of other excipients such as tea tree oil, cyclomethicone ($D_4$), tocopherol acetate etc. did not affect the physical stability of formulations as compositions appeared as clear oil solution.

Example: 2

Preparation of Various Oil Compositions Containing Ketoconazole

The compositions were prepared by dissolving the active agent in ethanol. The oleyl alcohol was then added and stirred until homogenous solution was obtained. Other excipients or additives were added and stirred to get clear solution except liquid paraffin. Weight was finally made up with liquid paraffin and stirred until homogenous solution was obtained. Final formulations were clear transparent oil solutions. Table 2 describes anti-fungal clear oil compositions containing ketoconazole as anti-fungal agent using various excipients or additives.
Result:
1. Compositions using liquid paraffin as base oil containing ketoconazole, were clear oil solutions.
2. Addition of other excipients such as tea tree oil, terpene-4-ol, caprylic acid, cyclomethicone ($D_4$) etc. did not affect the physical stability of formulations and compositions appeared as clear oil solution.

Example 3

Study of Oil Containing Fatty Acid/Esters as a Source of Nutrients for the Growth of *M. furfur* Under in vitro Condition

*Malassezia* species are lipophilic unipolar yeasts recognized as commensals of skin that may be pathogenic under certain conditions (*Indian Journal of Medical Microbiology*, (2004) 22 (3):179-181). To compare lipid requirements of the fungus most closely associated with dandruff/seborrheic dermatitis, the best studied *Malassezia* species is *M. furfur*. Lipid assimilation in vitro assay was designed to investigate lipid effect on growth of *M. furfur* (MTCC 1374).

Method: Briefly, Sabouraud Dextrose containing low-melt agar was melted, cooled to 38° C. Fatty acids/esters constituents eg, capric acid, caprylic acid, linoleic acid, oleic acid, lauric acid, palmitic acid, ethyl oleate, isopropyl myristate and oils containing fatty acid/esters eg, coconut oil, mustard oil etc., were added to study the growth of the fungus (Kaw Bing CHUA, et al *Malaysian J Pathol* (2005) 27(2): 99). After solidification, agar plates were streaked with *M. furfur* innoculum adjusted to appropriate cfu/ml, aseptically. Positive control with 2% olive oil and negative control without fatty substance were also maintained.
Results:
1. Results showed that there was no growth of *M. furfur* in absence of fatty acids/esters or oils in in vitro condition (FIG. 1) up to 6 days.
2. Culture media which contained fatty acids or esters eg, linoleic acid, oleic acid, lauric acid, palmitic acid, ethyl oleate, isopropyl myristate and oils containing fatty acid/esters eg, coconut oil, mustard oil etc. were showed confluent growth of fungus up to 6 days.
3. Culture media with lower carbon fatty acids ($C \leq 10$) eg, caprylic acid (C8) and capric (C10) were failed to provide nutrient for the growth of fungus and no growth was observed up to 6 days.

Example 4

Bioactivity of Oil Compositions Described in Example 1 Against *M. furfur*

The Minimum Inhibitory Concentration (MIC) is considered as an index for indicating Anti-fungal efficacy. Therefore lower the value of MIC of the composition, the better is its anti-fungal efficacy.

Method: The in vitro activities of some of the oil compositions containing piroctone olamine against *Malassezia furfur* (MTCC 1374) were determined by agar dilution methods (Jan Faergemann, et al *Acta Derm Venereol*, (2006), 86:312; Irith Wiegand, et al *Nature Protocols* (2008), 3:163) Appropriate dilutions of solubilized antifungal compositions were added to molten Leeming Notman Medium. Once the plates were set, *M. furfur* innoculum adjusted to appropriate cfu/ml was streaked on the agar plates and incubated for 6 days. After incubation, the plates were observed at day 3 and day 6 for visible *M. furfur* growth. The MIC is defined as as the lowest concentration of antifungal agents that inhibits visible growth of fungus.

Results:
1. Piroctone olamine containing oil compositions VPO-018, VPO-022, and VPO-028 with different solvents isopropyl alcohol, oleyl alcohol, and ethanol, respectively, showed MIC at 32 µg/ml which is similar to the MIC of positive control where drug is dissolved in DMSO at the same concentration as shown in Table 3.

Addition of other additives such as caprylic acid, cyclomethicone ($D_4$), tocopherol acetate etc. did not affect the MIC of oil compositions when used in concentration shown in table 1.

Example 5

Bioactivity of Oil Compositions Described in Example 2 Against *M. furfur*

Method: The in vitro activities of some of the oil compositions containing ketoconazole against *Malassezia furfur* (MTCC 1374) were determined by agar dilution methods. Appropriate dilutions of antifungal compositions were added to molten Leeming Notman Medium. Once the plates were set, *M. furfur* innoculum adjusted to appropriate cfu/ml was streaked on the agar plates and incubated for 6 days. After incubation, the plates were observed at day 3 and day 6 for visible *M. furfur* growth. The MIC is defined as the lowest tested dilution of antifungal active that yields no growth.

Result:
1. Ketoconazole containing oil compositions showed MIC at 0.25 µg/ml, which is similar to the MIC of positive control where drug is dissolved in DMSO at the same concentration as shown in Table 4.

Example 6

Effect of Various Fatty Acids/Esters on the in vitro Growth of *M. furfur*

A) Study of Various Oils Which are Glycerol or Glycol Esters (Less Than C-11 Carbon Number) on the Growth of *M. furfur* Under in vitro Conditions

*Malassezia* species are lipophilic, unipolar yeasts recognized as commensals of skin that may be pathogenic under certain conditions. To compare lipid requirements of the fungus most closely associated with dandruff/seborrheic dermatitis, the best studied *Malassezia* species is *M. furfur*. A lipid assimilation in vitro assay was designed to investigate lipid effect <C-11 fatty acid or their esters on growth of *M. furfur* (MTCC 1374).

Briefly, Sabouraud Dextrose containing low-melt agar was melted and cooled to 38° C. Fatty acids/esters constituents, e.g., caprylic acid, capric acid and Monocaprylate of propylene glycol, were added in 2% concentration to study the growth of the fungus. After solidification, agar plates were streaked with *M. furfur* innoculum adjusted to appropriate cfu/ml, aseptically. Positive control with 2% olive oil and negative control without fatty substance were also maintained.

Culture media with lower carbon fatty acids (less than C-11) such as caprylic acid (C-8) and capric acid (C-10) failed to serve as nutrients for the growth of fungus and no growth was observed for up to 6 days, while media supplemented with 2% olive oil showed confluent growth of fungus in the same duration. This is shown in FIG. 2.

B) Study of Various Oils Which are C-11 or Greater Fatty Acid or Their Esters on the Growth of *M. furfur* Under in vitro Conditions A lipid assimilation in vitro assay was designed to investigate lipid effect >C-10 fatty acid or their esters on growth of *M. furfur* (MTCC 1374). Sabouraud Dextrose containing low-melt agar was melted and cooled to 38° C. Fatty acids/esters constituents, e.g. fatty acids or esters, such as lauric acid, palmitic acid, myristic acid, oleic acid, linoleic acid, isopropyl myristate, ethyl oleate, mustard oils, coconut oil were added at different concentration to study the growth of the fungus. Positive control with 2% olive oil and negative control without fatty substance were also maintained. After solidification, agar plates were streaked with *M. furfur* innoculum adjusted to appropriate cfu/ml, aseptically.

Culture media with higher carbon fatty acids and esters (more than C-10) such as lauric acid, palmitic acid, myristic acid, oleic acid, linoleic acid, isopropyl myristate, ethyl oleate, showed confluent growth of fungus for up to 6 days. Interestingly vegetable oils such as mustard oils, coconut oil also showed confluent growth of *M. furfur* as shown in FIG. 3. In addition media supplemented with 2% olive oil showed confluent growth of fungus in the same duration while the media without oil supplement did not show any growth.

Example 7

Preparation of Oil Compositions Devoid of C-11 or Greater Fatty Acids/Esters Containing Antifungal Agent or Combination Thereof A) Preparation of Oil Compositions Devoid of C-11 or Greater Fatty Acids/Esters Containing Piroctone Olamine as Antifungal Agent.

These compositions were prepared by dissolving the active agent in ethanol or other suitable solvent. The oleyl alcohol was then added and stirred until a homogenous solution was obtained. Other excipients or additives were added and stirred to obtain a clear solution except liquid paraffin. The total volume was finally made up with liquid paraffin and stirred until homogenous solution was obtained. Final formulations were clear transparent oil solutions and coded as 1P, 2P, 3P and 4P as given in Table 5. All compositions are clear transparent solutions. In compositions 1P and 2P, caprylic acid was added to balance the pH of the formulations.

B) Study of MIC of Oil Compositions Devoid of C-11 or Greater Fatty Acids/Esters Containing Antifungal Agent Piroctone Olamine Against *M. furfur* Under in vitro Conditions.

As shown in Table 6 and Table 7, oil compositions containing piroctone olamine devoid of C-11 or greater fatty acids or their esters showed MIC in the range of 16-32 µg/ml against *M. furfur* and in the range of 8-16 µg/ml against *M. obtusa*. Composition having similar amount of piroctone olamine with 5% sunflower oil and 10% oleic acid were showed MIC at 64 µg/ml against both the strains. These results show that the presence of vegetable oil (sunflower) which is rich in triglycerides/free fatty acids above C-10, has an adverse effect on the activity of the antifungal agent. Similarly, the presence of fatty acids above C-10 (such as oleic acid) also has an adverse effect on the activity of the antifungal agent.

C) Preparation of Oil Compositions Devoid of C-11 or Greater Fatty Acids/Esters Containing Ketoconazole as Antifungal Agent.

These compositions were prepared by dissolving the active agent in ethanol or other suitable solvent. The oleyl alcohol was then added and stirred until a homogenous solution was obtained. Other excipients or additives were added and stirred to obtain a clear solution except liquid paraffin. The total volume was finally made up with liquid paraffin and stirred until homogenous solution was obtained. Final formulations were clear transparent oil solutions and coded as 1K, 2K, as given in Table 8. All compositions are clear transparent solutions.

D) Preparation of Oil Compositions Devoid of C-11 or Greater Fatty Acids/Esters Containing Piroctone Olamine and Ketoconazole as Antifungal Agents in Combination.

These compositions were prepared by dissolving the active agent in ethanol or other suitable solvent. The oleyl alcohol was then added and stirred until a homogenous solution was obtained. Other excipients or additives were added and stirred to obtain a clear solution except liquid paraffin. The total volume was finally made up with liquid paraffin and stirred until homogenous solution was obtained. Final formulations were clear transparent oil solutions and coded as 1PK, 2PK, as given in Table 9.

E) Preparation of Oil Compositions Devoid of C-11 or Greater Fatty Acids/Esters Containing Antifungal Agent with Hair Growth Promoter, Minoxidil.

The compositions were prepared as described above and coded as 1PM, 2PM and 3PM, as given in Table 10.

Example 8

A) Preparation of Various Gel Compositions Devoid of C-11 or Greater Fatty Acids/Esters Containing Different Antifungal Agents.

Initially, carbopol was added to the water and allowed to swell for 24 hours. Antidandruff agent was dissolved in minimum quantity of solvent and added to the carbopol base, followed by neutralization with a dilute aqueous solution of triethanolamine or sodium hydroxide to obtain pH 5.0-7.0. The gel compositions were coded as 1G, 2G, 3G, 4G, 5G and 6G as shown in Table 11.

B) Study of Zone of Inhibition (ZOI) of Gel Compositions Devoid of C-11 or Greater Fatty Acids/Esters Containing Antifungal Agent Piroctone Olamine Against *M. furfur* Under In Vitro Conditions.

To study the efficacy of gel compositions, ZOI was determination by Agar Well Diffusion method. Observations were shown in Table 12.

Results: As shown in Table 12, gel composition (1G) containing piroctone olamine showed ZOI (zone of inhibition) in the range of 1.2-0.9 cm against *M. furfur*. Whereas, composition (2G) with similar amount of piroctone olamine along with 4% propylene glycol mono caprylate showed ZOI 1.5-1.3 cm against *M. furfur*. After incorporation of 10% oleic acid with base formulation 1G, zone of inhibition was not observed. These results showed that the presence of oleic acid which is free fatty acids above C-10 has an adverse effect on the activity of the antifungal agent.

Example 9

Preparation of Various Cream Compositions Devoid of C-11 or Greater Fatty Acids/Esters Containing Different Antifungal Agents Creams were prepared by fusion method, where all oil soluble ingredients were weighed and melt at a temperature of 60-80° C. Aqueous phase was maintained at the same temperature and oil phase was poured into aqueous phase with constant stirring, followed by slow cooling with moderate stirring. The cream compositions were coded as 1C, 2C, 3C, 4C as shown in Table 13.

The antifungal compositions as disclosed in the invention are thus attained in a practical, and facile manner. While preferred aspects and example configurations have been shown and described, it is to be understood that various further modifications and additional configurations will be apparent to those skilled in the art. It is intended that the specific embodiments and configurations herein disclosed are illustrative of the preferred nature and best mode of practicing the invention, and should not be interpreted as limitations on the scope of the invention.

TABLE 1

Piroctone olamine-oil compositions

| Formula Code | PO (mg) | Ethanol (ml) | IPA (ml) | OA (ml) | Triacetin (ml) | Cap. A (ml) | Toco. Ace. (mg) | TTO (ml) | Cyclo-methicone ml | LLP ml, upto | pH | App |
|---|---|---|---|---|---|---|---|---|---|---|---|---|
| VPO-001 | 50 | 0.4 | — | 0.4 | — | 0.1 | — | 0.5 | — | 10 | 6-7 | C |
| VPO-002 | 50 | 0.4 | — | 0.4 | — | 0.1 | — | — | — | 10 | 6-7 | C |
| VPO-018 | 10 | — | 0.2 | 0.2 | — | 0.02 | — | — | — | 10 | 6-7 | C |
| VPO-019 | 10 | — | 0.2 | 0.2 | 0.02 | 0.02 | — | — | — | 10 | 6-7 | C |
| VPO-020 | 10 | — | 0.2 | 0.3 | 0.04 | 0.02 | — | — | — | 10 | 6-7 | C |
| VPO-021 | 10 | — | 0.2 | 0.5 | 0.06 | 0.02 | — | — | — | 10 | 6-7 | C |
| VPO-022 | 10 | — | — | 0.4 | — | 0.02 | — | — | — | 10 | 6-7 | C |
| VPO-023 | 10 | — | — | 0.4 | 0.02 | 0.02 | — | — | — | 10 | 6-7 | C |
| VPO-024 | 10 | — | — | 0.5 | 0.04 | 0.02 | — | — | — | 10 | 6-7 | C |
| VPO-025 | 10 | 0.05 | — | 0.05 | — | 0.02 | — | — | — | 10 | 6-7 | ST |
| VPO-026 | 10 | 0.05 | — | 0.3 | 0.02 | 0.02 | — | — | — | 10 | 6-7 | C |

TABLE 1-continued

Piroctone olamine-oil compositions

| Formula Code | PO (mg) | Ethanol (ml) | IPA (ml) | OA (ml) | Triacetin (ml) | Cap. A (ml) | Toco. Ace. (mg) | TTO (ml) | Cyclo-methicone ml | LLP ml, upto | pH | App |
|---|---|---|---|---|---|---|---|---|---|---|---|---|
| VPO-027 | 10 | 0.05 | — | 0.3 | 0.02 | 0.02 | — | 0.1 | — | 10 | 6-7 | C |
| VPO-028 | 10 | 0.05 | — | 0.1 | — | 0.02 | — | — | — | 10 | 6-7 | C |
| VPO-030 | 10 | — | 0.2 | 0.2 | — | 0.02 | — | — | 0.1 | 10 | 6-7 | C |
| VPO-031 | 10 | 0.05 | — | 0.1 | — | 0.02 | — | — | 0.1 | 10 | 6-7 | C |
| VPO-032 | 10 | — | 0.2 | 0.2 | — | 0.02 | — | — | 1.0 | 10 | 6-7 | C |
| VPO-023 | 10 | 0.05 | — | 0.1 | — | 0 02 | — | — | 1.0 | 10 | 6-7 | C |
| VPO-034 | 10 | — | 0.2 | 0.2 | — | 0.02 | 50 | — | — | 10 | 6-7 | C |
| VPO-035 | 10 | 0.05 | — | 0.1 | — | 0.02 | 100 | — | — | 10 | 6-7 | C |
| VPO-036 | 10 | — | 0.2 | 0.2 | — | 0.02 | 25 | — | — | 10 | 6-7 | C |
| VPO-037 | 10 | — | 0.2 | 0.2 | — | 0.02 | 50 | — | — | 10 | 6-7 | C |
| VPO-038 | 10 | — | 0.2 | 0.2 | — | 0.02 | 75 | — | — | 10 | 6-7 | C |
| VPO-039 | 10 | — | 0.2 | 0.2 | — | 0.02 | 100 | — | — | 10 | 6-7 | C |
| VPO-040 | 10 | — | 0.2 | 0.2 | — | 0.02 | 100 | — | 1.0 | 10 | 6-7 | C |
| VPO-041 | 10 | — | 0.2 | 0.2 | — | 0.02 | 100 | 0.2 | 1.0 | 10 | 6-7 | C |
| VPO-042 | 10 | 0.05 | — | 0.1 | — | 0.02 | 25 | — | — | 10 | 6-7 | C |
| VPO-043 | 10 | 0.05 | — | 0.1 | — | 0.02 | 50 | — | — | 10 | 6-7 | C |
| VPO-044 | 10 | 0.05 | — | 0.1 | — | 0.02 | 75 | — | — | 10 | 6-7 | C |
| VPO-045 | 10 | 0.05 | — | 0.1 | — | 0.02 | 100 | — | — | 10 | 6-7 | C |
| VPO-046 | 10 | 0.05 | — | 0.1 | — | 0.02 | 100 | — | 1.0 | 10 | 6-7 | C |
| VPO-047 | 10 | 0.05 | — | 0.1 | — | 0.02 | 100 | 0.2 | 1.0 | 10 | 6-7 | C |
| VPO-049 | 10 | — | — | — | — | 0.3 | — | — | — | 10 | 6-7 | C |
| VPO-050 | 10 | — | — | 0.2 | — | 0.2 | — | — | — | 10 | 6-7 | C |
| VPO-051 | 10 | — | — | — | — | 0.3 | 50 | 0.1 | 0.5 | 10 | 6-7 | C |
| VPO-052 | 10 | — | — | 0.1 | — | 0.3 | 50 | 0.2 | 0.5 | 10 | 6-7 | C |

C—Clear,
ST—Slight turbid,
PO—Piroctone olamine,
IPA—Isopropyl alcohol,
OA—oleyl alcohol,
Cap. A—Caprylic acid,
Toco. Ace.—Tocopherol acetate,
TTO—tea tree oil,
LLP—light liquid paraffin,
App—appearance

TABLE 2

Ketoconazole-oil compositions

| Formulation Code | Keto (mg) | Ethanol (ml) | Oleyl Alco (ml) | Caprylic acid (ml) | Tea Tree Oil (ml) | Terpene-4-01 (ml) | Tocopherol acetate (mg) | Cyclo-methicone (ml) | Liq. Paraffin (ml, upto) | pH | App. |
|---|---|---|---|---|---|---|---|---|---|---|---|
| VK-001 | 10 | 0.5 | 0.45 | — | 0.5 | — | — | — | 10 | 6-7 | C |
| VK-002 | 10 | 0.5 | 0.45 | — | — | — | — | — | 10 | 6-7 | C |
| VK-012 | 5 | 0.3 | 0.3 | — | — | — | — | — | 10 | 6-7 | C |
| VK-013 | 5 | 0.3 | 0.3 | — | 0.1 | — | — | — | 10 | 6-7 | C |
| VK-014 | 5 | 0.3 | 0.3 | — | 0.2 | — | — | — | 10 | 6-7 | C |
| VK-015 | 5 | 0.3 | 0.3 | — | 0.3 | — | — | — | 10 | 6-7 | C |
| VK-016 | 5 | 0.3 | 0.3 | — | 0.4 | — | — | — | 10 | 6-7 | C |
| VK-017 | 5 | 0.3 | 0.3 | — | 0.1 | — | — | 0.2 | 10 | 6-7 | C |
| VK-018 | 5 | 0.3 | 0.3 | — | 0.1 | — | — | 0.5 | 10 | 6-7 | C |
| VK-019 | 5 | 0.3 | 0.3 | — | 0.1 | — | — | 1.0 | 10 | 6-7 | C |
| VK-020 | 5 | 0.3 | 0.3 | — | — | — | — | 1.0 | 10 | 6-7 | C |
| VK-030 | 5 | — | 0.1 | 0.3 | — | 0.1 | 20 | — | 10 | 6-7 | ST |
| VK-031 | 5 | — | 0.1 | 0.3 | — | 0.2 | 20 | — | 10 | 6-7 | C |
| VK-032 | 5 | — | 0.1 | 0.3 | — | 0.3 | 20 | — | 10 | 6-7 | C |
| VK-036 | 5 | — | 0.1 | 0.4 | — | 0.1 | 20 | — | 10 | 6-7 | C |
| VK-037 | 5 | — | 0.1 | 0.4 | — | 0.2 | 20 | — | 10 | 6-7 | C |
| VK-038 | 5 | — | 0.1 | 0.4 | — | 0.3 | 20 | — | 10 | 6-7 | ST |
| VK-040 | 5 | — | 0.4 | 0.4 | — | 0.4 | 20 | — | 10 | 6-7 | C |

C—Clear transparent,
ST—Slight turbid

TABLE 3

Results of MIC for oil compositions of piroctone olamine

| Formulation Codes | Concentration (μg/ml) | | | |
|---|---|---|---|---|
| | 8 | 16 | 32 | 64 |
| VPO-001 | + | + | − | − |
| VPO-018 | + | + | − | − |
| VPO-022 | + | + | − | − |
| VPO-028 | + | + | − | − |
| VPO-030 | + | + | − | − |
| VPO-031 | + | + | − | − |
| VPO-032 | + | + | − | − |
| VPO-033 | + | + | − | − |
| VPO-034 | + | + | − | − |
| VPO-035 | + | + | − | − |
| VPO-NC (Negative control) | + | + | + | + |
| PO in DMSO (Positive control) | + | + | − | − |

"+" indicates growth of fungus and "−" indicates no growth of fungus

TABLE 4

Results of MIC for oil compositions of ketoconazole

| Formulation Codes | Concentration (μg/ml) | | | | | |
|---|---|---|---|---|---|---|
| | 0.0625 | 0.125 | 0.25 | 0.5 | 1 | 2 |
| VK-001 | + | + | − | − | − | − |
| VK-002 | + | + | − | − | − | − |
| VK-013 | + | + | − | − | − | − |
| VK-019 | + | + | − | − | − | − |
| VK-NC (Negative control) | + | + | + | + | + | + |
| Keto in DMSO (Positive control) | + | + | − | − | − | − |

"+" indicates growth of fungus and
"−" indicates no growth of fungus

TABLE 5

Oil compositions containing piroctone olamine as antifungal agent

| Ingredients | Compositions | | | |
|---|---|---|---|---|
| | 1P | 2P | 3P | 4P |
| Piroctone olamine (mg) | 50 | 50 | 50 | 50 |
| Oleyl alcohol (ml) | 0.5 | 0.5 | 2 | 3 |
| Ethanol (ml) | 0.3 | 0.3 | 0.75 | 0.75 |
| Caprylic acid (ml) | 0.08 | 0.08 | — | — |
| Propylene glycol mono caprylate (ml) | — | — | 4 | 4 |
| Tocopherol acetate (antioxidant) | q.s.* | q.s. | q.s. | q.s. |
| Butylated hydroxy toluene (Preservative) | q.s. | q.s. | q.s. | q.s. |
| Light liquid paraffin (ml, Up to) | 100 | 100 | 100 | 100 |

*q.s. Quantity sufficient

TABLE 6

MIC of oil compositions containing piroctone olamine against *M. furfur*

| Compositions | concentration (μg/ml) | | | |
|---|---|---|---|---|
| | 8 | 16 | 32 | 64 |
| 1P | + | + | − | − |
| 2P | + | + | − | − |
| 3P | + | − | − | − |
| 4P | + | − | − | − |
| Base formulation with 5% sunflower oil | + | + | + | − |
| Base formulation with 10% oleic acid | + | + | + | − |
| Piroctone olamine in DMSO (Positive control) | + | + | − | − |

"+" indicates growth of fungus and "−" indicates no growth of fungus

TABLE 7

MIC for oil compositions containing piroctone olamine against *M. obtusa*

| Compositions | Concentration (μg/ml) | | | | |
|---|---|---|---|---|---|
| | 4 | 8 | 16 | 32 | 64 |
| 1P | + | + | − | − | − |
| 2P | + | + | − | − | − |
| 3P | + | − | − | − | − |
| 4P | + | − | − | − | − |
| Base formulation with 5% sunflower oil | + | + | + | + | − |
| Base formulation with 10% oleic acid | + | + | + | + | − |
| Piroctone olamine in DMSO (positive control) | + | + | + | − | − |

"+" indicates growth of fungus and "−" indicates no growth of fungus

TABLE 8

Oil compositions containing ketoconazole as antifungal agent

| Ingredients | Compositions | |
|---|---|---|
| | 1K | 2K |
| Ketoconazole (mg) | 20 | 20 |
| Oleyl alcohol (ml) | 0.5 | 0.5 |
| Ethanol (ml) | 0.3 | 0.3 |
| Caprylic acid (ml) | 0.5 | 0.7 |
| Propylene glycol mono caprylate (ml) | 4 | 4 |
| Tocopherol acetate (antioxidant) | q.s. | q.s. |
| Butylated hydroxy toluene (Preservative) | q.s. | q.s. |
| Light liquid paraffin (ml, Up to) | 100 | 100 |

*q.s. Quantity sufficient

TABLE 9

Oil compositions containing piroctone olamine and ketoconazole in combination

| Ingredients | Compositions | |
|---|---|---|
| | 1PK | 2PK |
| Piroctone olamine (mg) | 50 | 50 |
| Ketoconazole (mg) | 20 | 20 |
| Oleyl alcohol (ml) | 2 | 2 |
| Ethanol (ml) | 1 | 1 |
| Caprylic acid (ml) | 0.1 | 0.1 |
| Propylene glycol mono caprylate (ml) | — | 4 |
| Tocopherol acetate (antioxidant) | q.s. | q.s. |
| Butylated hydroxy toluene (Preservative) | q.s. | q.s. |
| Light liquid paraffin (ml, Up to) | 100 | 100 |

*q.s. Quantity sufficient

TABLE 10

Oil compositions containing piroctone olamine as antifungal agent and Minoxidil

| Ingredients | Compositions | | |
|---|---|---|---|
| | 1PM | 2PM | 3PM |
| Minoxidil (mg) | 500 | 500 | 500 |
| Piroctone olamine (mg) | 50 | 50 | — |
| Ethanol (ml) | 10 | 15 | 20 |
| Propylene glycol | — | — | 10 |
| Oleyl alcohol (ml) | 10 | 20 | — |
| Caprylic Acid (ml) | 5.0 | 5.0 | — |
| Tocopherol Aetate (mg) | q.s. | q.s. | q.s. |
| Mono/diglycerides of caprylic acid (ml) | — | — | Up to 100 |
| Light liquid paraffin (ml, upto) | 100 | 100 | — |

*q.s. Quantity sufficient

TABLE 11

Gel compositions containing antifungal agents devoid of C-11 or greater fatty acids/esters

| Ingredients | Compositions (wt %) | | | | | |
|---|---|---|---|---|---|---|
| | 1G | 2G | 3G | 4G | 5G | 6G |
| Piroctone Olamine | 0.05 | 0.05 | 0.05 | 0.05 | — | — |
| Ketoconazole | — | — | — | — | — | 0.016 |
| Zinc Pyrithione | — | — | — | — | 0.016 | — |
| Ethanol | 10.0 | 4.0 | 4.0 | 4.0 | — | — |
| Propylene glycol | — | — | — | — | — | 10 |
| PEG-400 | — | — | — | — | 10.8 | — |
| Propylene glycol mono caprylate | — | 4.0 | 4.0 | 4.0 | 4.0 | 4.0 |
| Polymeric surfactant | — | 0.2 | 0.2 | 0.2 | 0.2 | 0.2 |
| Carbopols | 0.3 | 0.3 | 0.4 | 0.5 | 0.5 | 0.5 |
| Triethanolamine/ sodium hydroxide (pH adjuster) | q.s | q.s | q.s | q.s | q.s | q.s |
| Water | q.s. (Balance) | q.s. (Balance) | q.s. (Balance) | q.s. (Balance) | q.s. (Balance) | q.s. (Balance) |

*q.s. Quantity sufficient

TABLE 12

Zone of inhibition of gel compositions containing piroctone olamine against *M. furfur*

| Formulations | Zone of Inhibition (in cm) | | |
|---|---|---|---|
| | Setup1 | Setup2 | Setup3 |
| 1G | 1.2 | 1.0 | 0.9 |
| 2G | 1.4 | 1.5 | 1.3 |
| 1G with 10% oleic acid | — | — | — |
| Gel base without anti-fungal agent (negative control) | — | — | — |

TABLE 13

Preparation of cream compositions containing antifungal agents Piroctone olamine or ketoconazole.

| Ingredient | Compositions (% wt) | | | |
|---|---|---|---|---|
| | 1C | 2C | 3C | 4C |
| Piroctone Olamine | 0.05 | 0.1 | — | — |
| Ketoconazole | — | — | 2.0 | 1.0 |
| Lauryl alcohol | 6 | 6 | 6 | 6 |
| Steryl alcohol | 7 | 7 | 7 | 7 |
| Triglyceride of caprylic acid | 1.0 | 1.0 | 1.0 | 1.0 |
| Cyclomethicone | 7 | 7 | 7 | 7 |
| PEG2 ether of stearic acid | 0.5 | 0.5 | 0.5 | 0.5 |
| PEG21 ether of stearic acid | 2.5 | 2.5 | 2.5 | 2.5 |
| Propylene glycol | 5.0 | 5.0 | 5.0 | 5.0 |
| Carbopol | 0.25 | 0.25 | 0.25 | 0.25 |
| pH adjuster (sodium hydroxide or citric acid) | q.s. | q.s. | q.s. | q.s. |
| Water | q.s. (Balance) | q.s. (Balance) | q.s. (Balance) | q.s. (Balance) |

*q.s. Quantity sufficient

We claim:

1. An antifungal composition comprising:
   (i) at least one antifungal agent selected from the group consisting of terbinafine, butenafine, ketoconazole, zinc pyrithione, luliconazole, piroctone olamine, efinaconazole, and cyclopirox olamine; at least one oil, wherein said oil is a fatty acid or ester thereof having carbon chain length ranging from C-1 to C-10; and at least one excipient;
      wherein the fatty acid or ester having carbon chain length ranging from C-1 to C-10 is selected from the group consisting of propylene glycol monocaprylate and glyceryl monocaprylate,
      wherein said composition is devoid of C-11 or greater fatty acids and esters, and
      wherein the composition comprises from about 0.01% to about 10% of weight of said antifungal agent; or
   (ii) at least one antifungal agent selected from the group consisting of butenafine, ketoconazole, luliconazole, piroctone olamine, efinaconazole, cyclopirox and itraconazole; at least one oil, wherein said oil is a fatty acid or ester thereof having carbon chain length ranging from C-1 to C-10; and at least one excipient;
      wherein the fatty acid or ester having carbon chain length ranging from C-1 to C-10 is caprylic acid,
      wherein said composition is devoid of C-11 or greater fatty acids and esters, and
      wherein the composition comprises from about 0.01% to about 10% of weight of said antifungal agent.

2. The antifungal composition of claim 1, wherein the composition comprises about 0.01% to about 5% by weight of said antifungal agent.

3. The antifungal composition of claim 1, wherein: (i) said antifungal agent is piroctone olamine, ketoconazole, luliconazole, terbinafine, or zinc pyrithione, and the fatty acid or ester having carbon chain length ranging from C-1 to C-10 is selected from the group consisting of propylene glycol monocaprylate and glyceryl monocaprylate; or (ii) said antifungal agent is piroctone olamine, ketoconazole, itraconazole, luliconazole, or zinc pyrithione, and the fatty acid or ester having carbon chain length ranging from C-1 to C-10 is caprylic acid.

4. The antifungal composition of claim 3, wherein said antifungal agent is piroctone olamine.

5. The antifungal composition of claim 3, wherein said antifungal agent is ketoconazole.

6. The antifungal composition of claim 1, wherein said excipient is solvent, additive or a combination thereof.

7. The antifungal composition of claim 1, wherein the composition comprises about 0.5% to about 99% by weight of said excipient.

8. The antifungal composition of claim 1, wherein said composition is formulated into cream, oil, lotion, serum, gel, shampoo, nail varnish, ointment, foam, spray or aerosol.

9. The antifungal composition of claim 8, wherein said composition is anti-dandruff oil.

10. The antifungal composition of claim 9, wherein said antifungal agent is piroctone olamine.

11. A method for treatment of a fungal infection, comprising administering the antifungal composition of claim 1 to a subject in need thereof.

12. A method for preparing the antifungal composition of claim 1, said method comprising:
   a. adding at least one fatty acid or ester thereof having carbon chain length ranging from C-1 to C-10 to an antifungal composition which is free of C11 or greater fatty acid or ester thereof; or
   b. replacing a C11 or greater fatty acid or ester thereof, present in an antifungal composition, with at least one fatty acid or ester thereof having carbon chain length ranging from C-1 to C-10.

13. A method for reducing fungal growth using the antifungal composition of claim 1.

14. The antifungal composition of claim 1, wherein the fatty acid or ester having carbon chain length from C1 to C10 is caprylic acid.

15. The antifungal composition of claim 1, wherein the fatty acid or ester having carbon chain length from C1 to C10 is propylene glycol monocaprylate.

16. The antifungal composition of claim 1, wherein the fatty acid or ester having carbon chain length from C1 to C10 is glyceryl monocaprylate.

17. The antifungal composition of claim 3, wherein said antifungal agent is itraconazole, and the fatty acid or ester having carbon chain Dength ranging from C-1 to C-10 is caprylic acid.

18. The antifungal composition of claim 3, wherein said antifungal agent is luliconazole.

19. The antifungal composition of claim 3, wherein said antifungal agent is terbinafine, and the fatty acid or ester having carbon chain length ranging from C-1 to C-10 is selected from the group consisting of propylene glycol monocaprylate and glyceryl monocaprylate.

20. The antifungal composition of claim 3, wherein said antifungal agent is zinc pyrithione.

* * * * *

UNITED STATES PATENT AND TRADEMARK OFFICE
CERTIFICATE OF CORRECTION

PATENT NO. : 10,232,047 B2
APPLICATION NO. : 14/366755
DATED : March 19, 2019
INVENTOR(S) : Sudhanand Prasad et al.

It is certified that error appears in the above-identified patent and that said Letters Patent is hereby corrected as shown below:

In the Claims

In Claim 3, Column 19, Line 42, please replace "caprylie" with --caprylic--

In Claim 17, Column 20, Line 37, please replace "Dength" with --length--

Signed and Sealed this
Tenth Day of September, 2019

Andrei Iancu
*Director of the United States Patent and Trademark Office*